United States Patent [19]

Mercier et al.

[11] Patent Number: 5,679,879
[45] Date of Patent: Oct. 21, 1997

[54] PROCESS FOR THE PRODUCTION OF SUBSTITUTED AROMATIC HYDROCARBONS FROM CORRESPONDING ANILINES BY DEDIAZONIATION

[75] Inventors: Claude Mercier, Knoll Hill; Graham Vaughan Scott, Chew-Magna, both of United Kingdom

[73] Assignee: Rhone-Poulenc Chemicals Limited, Hertfordshire, United Kingdom

[21] Appl. No.: 372,040

[22] Filed: Jan. 12, 1995

[30] Foreign Application Priority Data

Jan. 13, 1994 [GB] United Kingdom ............... 9400569

[51] Int. Cl.$^6$ ................................................ C07C 1/20
[52] U.S. Cl. ................................... 585/469; 585/408
[58] Field of Search ............................... 585/469, 408

[56] References Cited

U.S. PATENT DOCUMENTS

| | | | |
|---|---|---|---|
| 3,707,562 | 12/1972 | Schindler | 585/469 |
| 3,894,107 | 7/1975 | Butter et al. | 585/469 |
| 4,508,784 | 4/1985 | Gugliemetti | 585/469 |
| 4,577,046 | 3/1986 | Hylarides et al. | 585/469 |
| 5,475,176 | 12/1995 | Beller et al. | 585/469 |

*Primary Examiner*—Helane Myers
*Attorney, Agent, or Firm*—Burns, Doane, Swecker & Mathis, L.L.P.

[57] ABSTRACT

Substituted aromatic hydrocarbons, e.g. 1,3-difluorobenzene, are produced by dediazoniation of the corresponding aromatic primary amines by converting them into a corresponding diazonium salt in the presence of hypophosphorous acid and a metal catalyst so that the diazonium group is replaced by hydrogen as it is formed.

14 Claims, No Drawings

PROCESS FOR THE PRODUCTION OF SUBSTITUTED AROMATIC HYDROCARBONS FROM CORRESPONDING ANILINES BY DEDIAZONIATION

This invention relates to the production of aromatic hydrocarbons.

It is well known to replace aromatic primary amino groups by hydrogen by converting the amino group into a corresponding diazonium salt group and then reducing the latter. For this purpose a number of reducing agents have been used, including hypophosphorous acid ($H_3PO_2$) and primary alcohols. A metallic catalyst, e.g. copper or one of its salts, is usually included in the reaction mixture to promote the reduction.

1,3-Difluorobenzene is an important intermediate in the preparation of antifungal agents, and it has often been prepared from 2,4-difluoroaniline by diazotisation followed by reducing dediazoniation. Japanese Patent Application 91/34944 (Tokemu Product K.K., Chemical Abstracts 115: 28858c) describes the production of 1,3-difluorobenzene by diazotization of 2,4-difluoroaniline and reductive dediazoniation with hypophosphorous acid in the presence of more than 2 moles of acid (3 moles in the Examples). In another process, the reduction has been effected with isopropanol in the presence of a copper catalyst.

These processes have significant disadvantages in practical use. Diazonium salts are unstable and can decompose violently in the solid or concentrated form. The handling of diazonium salts in substantial quantities on an industrial scale requires special precautions to prevent accident. Moreover, the known processes produce significant quantities of effluent which requires treatment (e.g. to reduce its copper content) before it can be discharged. There is therefore a need for a process which can be operated easily on an industrial scale with reduced risk and reduced quantities of effluent.

We have now devised a process in which the diazotization of substituted aromatic primary amines is carried out in the presence of hypophosphorous acid and a suitable metal catalyst so that the diazonium salt group formed is immediately replaced by hydrogen. The reaction mixture thus never contains any substantial quantity of diazonium salt. Moreover, reduced quantities of reagents, especially catalyst and mineral acid, are used, and this very considerably simplifies the handling of the effluents produced by the process, and its volumic productivity is increased.

An improved method for the isolation of the substituted aromatic hydrocarbon has also been devised which makes it possible to obtain a product of high purity in a very simple way.

The process of the present invention for the production of a substituted aromatic hydrocarbon from a corresponding substituted aromatic primary amine comprises converting the said amine into a corresponding diazonium salt in the presence of hypophosphorous acid or a hypophosphite salt and a strong acid (i.e. an acid having a pKa less than or equal to 0) in an amount not greater than that required to convert the amine into an acid addition salt thereof and to convert a said hypophosphite salt (if used) into hypophosphorous acid, and a metal catalyst, e.g. a copper or iron catalyst, so that the diazonium group is replaced by hydrogen as it is formed.

The new process is especially useful for the production of substituted aromatic hydrocarbons such as the 1,3-difluorobenzene already mentioned. Thus, in its preferred operation, the new process involves the conversion of a starting material of formula:

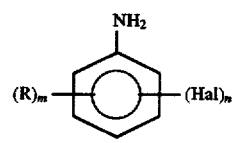

where R is alkyl, alkoxy or alkylthio each of which has up to 4 carbon atoms and is unsubstituted or substituted by halogen, e.g. methyl, trifluoromethyl, trifluoromethoxy, or trifluoromethylthio, Hal is fluorine, chlorine or bromine, m is 0 to 4, and n is 1 to 5, the Hal radicals being the same or different when n is 2 to 5, and the sum of m and n being 1 to 5, into a product of the formula:

where Hal, m and n are as hereinbefore defined.

The diazotisation of the aromatic amine is carried out with reagents of known kind. Thus the amine, in the presence of a suitable strong mineral acid, preferably an oxygen-containing acid such as sulphuric acid, may be treated with an alkali metal nitrite, e.g. sodium nitrate. Since, in the process of the invention, the diazotisation is carried out in the presence of hypophosphorous acid ($H_3PO_2$), the latter may be used to convert the alkali metal nitrite into nitrous acid. The reduction of the diazonium salt to replace the diazonium group by hydrogen requires 1 mole of hypophosphorous acid per mole of starting amine (i.e. per amino group to be replaced by hydrogen). In principle, therefore, 1 mole of hypophosphorous acid per mole of starting amine can be used both to convert the required amount of alkali metal nitrite into nitrous acid, and to reduce the diazonium group. However, An practice, a moderate excess of acid (preferably not more than 1.33 mole per amino group to be replaced) should be used. If hypophosphorous acid As used as the sole mineral acid, 1 to 2 moles per mole of starting amine are used, while if a strong mineral acid is also included in the reaction mixture, then the proportion of hypophosphorous acid may be reduced, but not below 1 molar proportion per amino group to be replaced, and the amount of the strong acid may be 0 to 1 equivalent per mole of starting amine. It is to be noted in this connection that sulphuric acid behaves in the context of the present invention as a monobasic acid as its second dissociation constant is not that of a strong acid as defined above.

If the hypophosphorous acid is introduced in the form of a salt, e.g. $NaH_2PO_2$, 1 equivalent of strong mineral acid is required to convert this salt into hypophosphorous acid, and one equivalent of the strong acid is also required to convert the alkali metal nitrite into nitrous acid. In no case are more than 2 equivalents of total acids used per mole of amine.

The reaction may be operated at a temperature in the range of 10° to 80° C. At temperatures below about 10° C., the reaction proceeds only slowly even in the presence of the catalyst. At above 80° C., the reaction may be difficult to control. A preferred temperature range is 20° to 50° C. A metal catalyst based on, for example, iron or preferably copper is included in the reaction mixture. The proportion of copper catalyst required is only 0.001 to 0.1 moles of copper, preferably about 0.005 moles, per mole of the aromatic amine starting material. The copper catalyst is conveniently added in the form of a cupric salt, e.g. cupric sulphate, but can, if desired, be added in other forms, e.g. as cuprous oxide ($Cu_2O$) or even finely divided metallic copper.

The reaction is preferably operated by forming a reaction mixture comprising aqueous hypophosphorous acid (as such or as a salt), e.g. in a proportion of 1.00 to 1.3 moles per mole of the amine to be used, and sulphuric acid in a proportion of 0.25 to 0.5 moles per mole of amine (plus any amount required to convert a salt of hypophosphorous acid into the free acid). To this mixture, the copper catalyst, e.g. cuptic sulphate, is added in a proportion of 0.002 to 0.01 moles per mole of amine. The total amount of water included in the mixture should be enough for a readily stirrable reaction mixture to be obtained, but is preferably not much greater than this. It may be, more particularly, about 30 to 50% of the total weight of the acids used. Typically 100 to 400 g, preferably 150 to 300 g, of water are used per mole of amine starting material. This mixture is adjusted to the required temperature, e.g. 25° C.

The aromatic primary amine starting material, e.g. 2,4-difluoroaniline, preferably as the free base, but if desired as a salt (preferably with a strong mineral acid), and the sodium nitrite, as a concentrated aqueous solution (containing e.g. 30 to 70% by weight of the nitrite), in an amount from 1 to 1.1 moles per mole of the amine, are then added alternately in portions not exceeding 50%, preferably 10% to 33%, by weight of the whole. Continuous simultaneous addition of the solutions is also possible the rates being adjusted so that a small excess of the amine (relative to the nitrite) is maintained in the reaction mixture. In the reaction mixture the amine is present in the form of a salt having only limited solubility, and the concentration of the amine is preferably as high as possible consistent with obtaining a stirrable reaction mixture.

The rate of mixing of the solutions is adjusted so that there is no build up of diazonium salt in the reaction mixture and substantially immediate reduction of the diazonium salt promoted by the presence of the catalyst. Desirably, the detectable concentration of diazonium salt in the reaction mixture is maintained below about 0.05 moles per litre, and preferably at 0.001–0.005 moles per litre.

The mixture obtained after the reaction consists of an organic phase containing the desired substituted aromatic hydrocarbon which is substantially insoluble in water, and an aqueous phase containing the residues of the acids and inorganic compounds used. If desired, and if its boiling point permits it, the substituted aromatic hydrocarbon product may be distilled from the reaction mixture as it is formed.

According to a feature of the invention, the reaction product is conveniently worked up by adding thereto a water-immiscible aliphatic alcohol having a boiling point above 150° C., e.g. 2-ethyl-1-hexanol (b.p. 183° C.), preferably after the non-aqueous phase (containing most of the desired product) has been separated. The water-immiscible phase containing the desired substituted aromatic hydrocarbon and the alcohol is then separated from the aqueous residue of the reaction medium and optionally washed to remove residual acid. This organic phase (which may then be recombined with the non-aqueous phase from the reaction mixture) is then fractionally distilled in the presence of a small amount of water. The substituted aromatic hydrocarbon forms an azeotrope with water and this azeotrope is collected. Since the substituted aromatic hydrocarbon is substantially insoluble in water, the azeotrope separates into two phases, and of these the organic phase is the desired product in substantially pure form. It may, if desired, be dried and redistilled before use.

The aliphatic alcohol can be recovered from the distillation residue and reused.

When the process is operated in glass vessels, a hydrofluoric acid trap such as boric acid may be included in the reaction mixture to trap fluoride ions and prevent corrosion of the apparatus.

The following Examples illustrate the invention. The stated molar proportions are in relation to the amine starting material.

EXAMPLES

Example 1 (0.875 mole DFA with 1 molar proportion $H_3PO_2$+0.5 molar proportion $H_2SO_4$.)

Into a 500 ml flask fitted with an addition funnel, thermometer mechanical stirrer and a 4' column fractionation apparatus fitted on top with a gas counter, hypophosphorous acid (50% w/w aqueous, 115.2 g, 1.0 molar proportion), copper sulphate pentahydrate (1.12 g, 0.005 molar proportion) and boric acid (0.54 g, 0.001 molar proportions) were introduced. To the pale blue solution at 25° C., 77% $H_2SO_4$ (56 g, 0.5 molar proportion) was added. The reaction was moderately exothermic. The temperature was maintained <50° C. with ice cooling. ⅓ of the 2,4-difluoroaniline (total weight 2,4 DFA=113 g=87 ml, i.e. ⅓=~29 ml.) was added dropwise, while maintaining vigorous stirring at temperature <30° C. A mobile slurry was obtained. To the mixture, at 20°–30° C., a solution of one third of the total amount of sodium nitrite [total required is: 63 g $NaNO_2$, i.e. 1.05 molar proportion, in 105 g of water, for 125 ml total volume, so ⅓ portion is ~40 ml.] was added, while maintaining vigorous stirring and a temperature between 20°–30° C. (ice bath). Typical addition time was ~30 mn. Nitrogen was evolved immediately (and measured with a gas counter). At the end of the addition of the first portion of sodium nitrite, the reaction mixture was kept for a few minutes until the end of gas evolution and the second portion of 2,4-difluoroaniline was then added followed by the second part of the sodium nitrite solution. Finally the last portions of the 2,4-DFA and the sodium nitrite were added.

At the end of the addition, the top organic phase (brown) was separated from the bottom aqueous layer. The aqueous layer was extracted with 2×10 ml of 2-ethyl-1-hexanol (d=0.8). All the organic phases (107.1 g) were combined and washed with a 10% ammonium chloride solution until neutral. After atmospheric pressure distillation (b.p. of 1,3-difluorobenzene azeotrope with water=72° C./760 mmHg) and decantation to separate the aqueous phase from 1,3-DFB, 81.9 g of pure 1,3 DFB (purity ≧99.8% by GC) were obtained, i.e. a yield of 82%.

Example 2 (1.2 molar proportion $H_3PO_2$+0.5 molar proportion $H_2SO_4$)

The reaction was carried out as in Example 1 but using 1.2 molar proportion $H_3PO_2$ (138.25 g, 50% aqueous solution). After addition in 3 portions of the DFA and the sodium nitrite, the decantation/extraction gave 107.5 g of crude organics. After azeotropic distillation 82.3 g of colourless pure 1,3-DFB (99.8% by GC) were obtained, (yield ~82.5%).

Example 3 (0.4 molar proportion $NaH_2PO_2$+0.6 molar proportion $H_3PO_2$+1.0 molar proportion $H_2SO_4$)

The reaction was carried out as in Example 1 but with partial in situ generation of $H_3PO_2$ (from $NaH_2PO_2$ and $H_2SO_4$). After addition in 3 portions of the 2,4-DFA and the sodium nitrite solutions, 21.1 l of gas evolved. The decantation/extraction gave 101.1 g of crude organics. After azeotropic distillation, 75.1 g of pure 1,3-DFB were obtained (yield ~75.2%).

Example 4 (1.0 molar proportion $NaH_2PO_2$+1.5 molar proportion $H_2SO_4$)

The reaction was carried out as in Example 1 but with total in situ generation of $H_3PO_2$. After addition of the starting materials in 3 portions, 20.4 l of gas evolved. The decantation/extraction gave 104.4 g of crude organics. After azeotropic distillation, 70.2 g of pure 1,3-DFB were obtained. (Yield ~70.4%).

Example 5

The reaction was carried out as in Example 1 but with a reaction temperature of 50° C.±5° C. 21.9 L of gas were evolved in 1 hour 30 minutes. The decantation/extraction gave 104.95 g of crude organics. After azeotropic distillation, 74.3 g of colourless 1,3-DFB (74.5% yield) were obtained.

Comparative Example 2,4 Difluoroaniline sulfate was prepared by mixing 62.6 g (2.5 molar proportions) of 98% sulphuric acid with 32.3 g (0.25 mole) of 2,4-difluoroaniline in a three neck flask. 66 g (2.0 molar proportions) of 50% $H_3PO_2$ aqueous solution were added and the slurry was allowed to warm to 50° C.±5° C. Then 18.3 g (1.1 molar proportion) of sodium nitrite dissolved into 30 g of water were added drop by drop, while the temperature was kept at 50° C.±5° C. After 1 hour 30 minutes for the complete addition, only 3.2 liter of gas had been evolved (Theory [~6.3 l). The reaction mixture was worked up as in Example 1 (decantation, extraction, distillation). Only 7.7 g of 1,3-difluorobenzene (yield=27%) were obtained.

Example 6

The reaction was carried out as in Example 1 but using different anilines as starting materials. The Table below summarises the yields obtained after isolation by decantation, extraction and distillation : (not optimised).

| Substrate | Product | Yield (isolated-Pure) |
|---|---|---|
| Bromo-6-difluoro-2,4-aniline | Bromo-1-difluoro-3,5-benzene | 72% |
| m.Trifluoromethylaniline | Trifluoromethyl benzene | 79% |
| 4-Chloro-2-fluoroaniline | 3-Chlorofluorobenzene | 81% |
| 2,6-Difluoroaniline | 1,3-Difluorobenzene | 77% |
| 2,4-Difluoroaniline (80%) + 2,6-Difluoroaniline (20%) | 1,3-Difluorobenzene | 78% |
| Trifluoro-2,3,4-aniline | Trifluoro-1,2,3-benzene | 82% |
| Pentafluoroaniline | Pentafluorobenzene | 83% |
| p.Trifluoromethyoxy aniline | Trifluoromethoxy benzene | 70% |
| 2-Flouro-5-methyl aniline | 4-Fluorotoluene | 84% |

Example 7

(Industrial production)

In a 1.3 m³ glass lined reactor under nitrogen, 335 kg 50% $H_3PO_2$ and 160.5 kg $H_2SO_4$ (77%) were charged on a mixture containing 104 kg of a 2% w/w boric acid aqueous solution and 22.5 kg of a 15% w/w copper sulphate aqueous solution.

324 kg of 2,4-difluoroaniline was added (in 3 steps) alternatively with 487 kg of 40% w/w sodium nitrite aqueous solution at a temperature controlled to be 25°–30° C. whilst controlling instantaneous decomposition of the diazonium salt by nitrogen evolution. At the end of the nitrite addition (63 kg of nitrogen evolved), decantation and extraction of the aqueous phase by 30 kg of ethyl hexanol gave 352 kg of crude 1,3DFB. The aqueous phase (1040 kg) contained only 0.6 kg of 1,3DF (GC analysis).

Distillation at atmosphere pressure of the crudes gave a 82.3% yield on grade 1,3DFB. (99.8% Purity by GC—500 ppm water).

We claim:

1. In a process for the production of a substituted aromatic hydrocarbon from a corresponding substituted aromatic primary amine which comprises converting said amine into a corresponding diazonium salt in the presence of hypophosphorous acid or a hypophosphite salt, a strong acid and a metal catalyst, so that the diazonium group is replaced by hydrogen as it is formed, the improvement comprising employing the strong acid in an amount not greater than that required to convert the amine into an acid addition salt thereof and to convert a said hypophosphite salt, if used, into hypophosphorous acid.

2. Process according to claim 1 wherein the starting material has the formula:

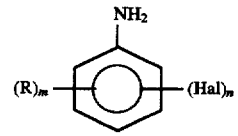

where R is alkyl, alkoxy or alkylthio, each of which has up to 4 carbon atoms and is unsubstituted or substituted by halogen, Hal is fluorine, chlorine or bromine, m is 0 to 4 and n is 1 to 5, the Hal radicals being the same or different when n is 2 to 5, and the sum of m and n being 1 to 5 and the product has the formula:

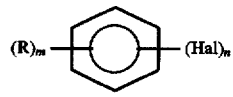

where R, Hal, m and n, are as hereinbefore defined.

3. Process according to claim 2 wherein the aromatic amine starting material is 2,4-difluoroaniline.

4. Process according to claim 2, wherein the said further mineral acid is sulphuric acid.

5. Process according to claim 2 wherein the reaction is performed at 10° to 80° C.

6. Process according to claim 5 wherein the reaction is performed at 20° to 50° C.

7. Process according to claim 1 wherein the said amine is converted into a corresponding diazonium salt by reaction in aqueous medium with a source of nitrite ion in the presence of hypophosphorous acid.

8. Process according to claim 4 wherein the said amine is reacted with an alkali metal nitrite in substantially equimolar amount in the presence of 1 to 2 molar proportions of hypophosphorous acid and 0 to 2 equivalents of a strong mineral acid, the total proportion of acid being not more than 2 equivalents per mole of said amine.

9. Process according to claim 4, wherein the amine and the nitrite are added either alternately to the reaction mixture in portions each of which constitutes 10 to 33% by weight of the whole or simultaneously and continuously in proportions such that a small excess of the amine is maintained in the reaction mixture.

10. Process according to claim 4 wherein the reaction in aqueous medium with the source of nitrite ion is in the presence of the hypophosphorous acid and a strong mineral acid.

11. Process according to claim 1 wherein the metal catalyst is a copper catalyst.

12. Process according to claim 8 wherein the proportion of the catalyst is 0.001 to 0.1 moles of copper per mole of the aromatic amine.

13. Process according to claim 1 wherein the substituted aromatic hydrocarbon product is separated from the reaction mixture by (i) extracting the aqueous phase of the reaction mixture with a water-immiscible aliphatic alcohol having a boiling point above 150° C., (ii) separating the extract obtained and, if desired, combining it with the previously separated water-immiscible phase of the reaction mixture, (iii) fractionally distilling the separated water-immiscible phase obtained in the presence of a small amount of water and collecting a fraction comprising an azeotropic mixture of water and the desired substituted aromatic hydrocarbon, and (iv) separating the substituted aromatic hydrocarbon from the said azeotropic mixture.

14. Process according to claim 12 wherein the said alcohol is 2-ethyl-1-hexanol.

* * * * *